United States Patent [19]

Kitamori et al.

[11] 4,036,948

[45] July 19, 1977

[54] L-ASCORBIC ACID TABLETS

[75] Inventors: Nobuyuki Kitamori, Suita; Tadashi Makino, Takatsuki; Keiji Hemmi, Toyono, all of Japan

[73] Assignee: Takeda Chemical Industries, Ltd., Osaka, Japan

[21] Appl. No.: 610,003

[22] Filed: Sept. 3, 1975

[30] Foreign Application Priority Data

July 24, 1975  Japan .................................. 50-90742

[51] Int. Cl.$^2$ .......................... A61K 9/32; A61K 9/00; A61K 31/375
[52] U.S. Cl. .......................................... 424/32; 424/16; 424/35; 424/37; 424/280
[58] Field of Search ...................... 424/280, 16, 35, 32, 424/37

[56] References Cited

U.S. PATENT DOCUMENTS

| | | | |
|---|---|---|---|
| 2,980,589 | 4/1961 | Grunigen | 424/280 |
| 3,084,104 | 4/1963 | Tuerck et al. | 424/280 |
| 3,584,114 | 6/1971 | Cavalli et al. | 424/280 |
| 3,639,168 | 2/1972 | Monti et al. | 424/280 |
| 3,873,713 | 3/1975 | Haas et al. | 424/280 |

*Primary Examiner*—Sam Rosen
*Attorney, Agent, or Firm*—Wenderoth, Lind & Ponack

[57] ABSTRACT

L-ascorbic acid tablets which contain more than about 90 weight percent of L-ascorbic acid and have a satisfactory mechanical strength can be obtained by spray-coating L-ascorbic acid powder capable of passing through a 200-mesh screen, with a solution of a binder under constant agitation in fluidized-bed granulating apparatus, until the amount of the binder has reached about 2 to about 4 weight percent relative to L-ascorbic acid, and compressing the resultant granules mixed with a lubricant into tablets.

9 Claims, No Drawings

L-ASCORBIC ACID TABLETS

The present invention relates to the production of L-ascorbic acid granules excellent in fluidity and homogeneity and to the improvement of L-ascorbic acid-containing tablets (the tablet is briefly referred to as L-ascorbic acid tablets).

High L-ascorbic acid content and practically satisfactory hardness or strength of product have been the essential requirements for L-ascorbic acid tablets. In the past, however, these two requirements were antagonistic to each other because for the enhancement of the strength of the tablet, the addition of a large amount of adjuvant or excipient is necessary, which results in the necessity of imposing an upper limit on the L-ascorbic acid content of the tablet. This upper limit must be imposed on the L-ascorbic acid content, since otherwise the large amounts of the ascorbic acid component required in high potency tablets, for example, coupled with the large amount of adjuvant required, would make the tablets too large to be comfortably swallowed by a person.

U.S. Pat. No. 3,453,368 is directed towards solving the aforementioned problems, but has not been satisfactory. The patent relates to a process for producing L-ascorbic acid tablets which comprises mixing 85 to 95 weight percent of L-ascorbic acid with 5 to 15 weight percent of modified starch or pregelatinized starch, followed by massing, crushing and drying in that order to give L-ascorbic acid-containing granules, and then mixing the resultant granules with a lubricant and compressing the mixture into tablets (hereafter briefly called wet-granulation process).

However, it is difficult to provide granules of good fluidity and homogeneity from said wet granulation process and, as a result, L-ascorbic acid tablets which are compressed from such granules are far from satisfactory in their mechanical strength (i.e., tensile strength or hardness).

In an attempt to overcome the drawbacks of the known arts and to provide an improved technique for preparing L-ascorbic acid granules fit to tablet, the present inventors have made an extensive research which culminated in the present invention.

Thus, one object of the present invention is to provide L-ascorbic acid granules as the material for the production of L-ascorbic acid tablets and to provide a process for producing such L-ascorbic acid granules. The other object of the present invention is to provide L-ascorbic acid tablets of high L-ascorbic acid content and high mechanical strength.

Further objects will be explained in the ensuing paragraphs.

As the first step of the process of the present invention, said L-ascorbic acid granules are prepared in the following manner. Thus, L-ascorbic acid powder, which passes through a 200-mesh screen, is spray coated with a solution of a binder under continuously fluidizing conditions.

In the present invention, use is made of L-ascorbic acid powder which passes through a 200-mesh screen and preferably not lower than 50 weight percent of which passes through a 325-mesh screen. Here "mesh" means that of W. S. Tyler Standard and "powder" includes ground as well as unground powder.

As the binder, there may be mentioned water-soluble binders such as pregelatinized starch (e.g., pregelatinized corn starch, pregelatinized white potato starch), pregelatinized modified starch (see code of Federal Regulation (U.S.A.) Para. 121,1031, a,b,c,d,e,f,g, and h), water-soluble celluloses (e.g. hydroxypropyl-cellulose, hydroxymethyl-cellulose, hydroxypropylmethyl-cellulose, carboxymethyl-cellulose), polyvinylpyrrolidone, polyvinyl alcohol, dextrin, gum arabicum and gelatin, organic solvent-soluble binders, such as cellulose derivatives (e.g., cellulose acetate phthalate, hydroxypropylmethyl-cellulose phthalate, ethyl-cellulose).

As the solvent for preparing the solution for spray-coating, there may be mentioned, for example, water, alcohols (e.g., methyl alcohol, ethyl alcohol, isopropyl alcohol), and acetone.

The concentration of the binder in the solution for spray-coating is rather optional but practically ranges from about 1 to about 10 weight percent, and preferably about 2 to about 8 weight percent.

The said fluidized-bed granulating apparatus comprises a fluidized-bed drying device fitted with spray means to inject a mist of a binder in such a manner that the granulating and drying operations may be accomplished in a single setup. By way of examples, Glatt (made by Glatt AG, West Germany), Aeromatic (made by Aeromatic AG, Switzerland), Calmic (made by Calmic Engineering Co., England), Growmax (made by Fuji Powdal Co., Japan) or Flowcoater (made by Freund Industries Co., Japan) are mentioned.

The granulating process continues until the amount of the binder has reached about 2 to about 4 weight percent relative to L-ascorbic acid.

As the second step of the process of the present invention, thus-prepared L-ascorbic acid granules are mixed with a lubricant and compressed into tablets.

As the lubricant use is made, for instance, of stearates (e.g., magnesium stearate, calcium stearate, stearic acid), corn starch and so on.

The amount and the kind of the lubricant are optionally selected from per se known lubricating compounds, but as the amount about 1 to about 7 weight percent relative to the L-ascorbic acid is recommended and as the kind of lubricant preferred, the addition of at least about 1 weight percent (relative to L-ascorbic acid), of stearates is most desirable.

In accordance with the method of this invention, L-ascorbic acid powder is homogeneously coated with a rather small amount of binder and the thus-obtained L-ascorbic acid granules are substantially free from fine dusts of the raw materials and are excellent in fluidity and may be easily mixed with other components. Besides, the L-ascorbic acid component in the granules remains stable, since moisture is highly detrimental to L-ascorbic acid, and applicants eliminate this problem by coating the granules with only a small amount of a moisture-absorbing binder.

The granules obtained by the present method are differentiated from the granules obtained by a wet-granulating method in electron microscopic photographs.

The above merits of the present granules, combine to contribute to the improvement of the final L-ascorbic acid tablets. Thus, the tablets prepared from the thus-obtained L-ascorbic acid granules are excellent in terms of L-ascorbic acid content and mechanical strength. The tablets can contain as high as about 90 to about 97.1 weight percent per tablet of L-ascorbic acid, while maintaining a tensile strength not lower than 12.5 kg/cm². In terms of L-ascorbic acid content per tablet, the range is from about 100 to about 2000 mg., more preferably about 400 to about 600mg.

In terms of disintegration, the tablets are satisfactory in that the disintegration time of the tablets falls within the requirements of the standards set in the Japanese Pharmacopoeia, 8th Edition.

The following examples and tests are further illustrative of this invention. In the examples and tests, "part(s)" and "percent(s)" are based on weight, unless otherwise specified.

The relationship between hardness and tensile strength of a tablet is shown by the following equation:

$$\sigma = (2P/\pi DT) \, (Kg/cm^2)$$

wherein $\sigma$ stands for tensile strength, $P$ for hardness, $D$ for diameter, $T$ for thickness and $\pi$ for circular constant, respectively. For practical use, tablets having a tensile strength of no lower than 12.5 kg/cm² is satisfactory.

EXAMPLE 1 a. 97 parts of ground powdery L-ascorbinc acid, which passed through a 200-mesh screen, 4.5 weight percent of which remained over a 250-mesh screen, but 82.8 weight percent of which passed through a 325-mesh screen, were sprayed under constant agitation in a fluidized-bed granulator with a paste which had been prepared by gelatinizing a 5.0 weight percent aqueous suspension of corn starch at 85° C and cooling to 50° C, until the coating amount of starch had reached 3 parts, followed by drying in situ. The product was then comminuted in a Fitz-mill, equipped with a 1.0 mm-screen, to obtain L-ascorbic acid granules.

b. 1. To 515 parts of the granules prepared as above there were added 5 parts of magnesium stearate and 15 parts of corn starch, and after mixing, the composition was compressed into a 535 mg. tablet.
L-ascorbic acid content: 93.5 weight percent
Hardness: 12.1 kg
Tensile strength: 18.4 kg/cm² b. 2. To 515 parts of the granules prepared as above (a) there were added 5 parts of magnesium stearate, and after mixing, the composition was compressed into a 520 mg. tablet.
L-ascorbic acid content: 96.2 weight percent
Hardness: 11.5 kg
Tensile strength: 17.5 kg/cm² b. 3. To 515 parts of the granules prepared as above (a) there were added 5 parts of magnesium stearate and 30 parts of corn starch, and after mixing, the composition was compressed into a 550 mg tablet.
L-ascorbic acid content: 90.9 weight percent
Hardness: 11.8 kg.
Tensile strength: 18.0 kg/cm²

EXAMPLE 2 a. 98 parts of ground powdery L-ascorbic acid which passed through a 200-mesh screen, 4.5 weight percent of which remained over a 250-mesh screen but 82.8 weight percent of which passed through a 325-mesh screen, were sprayed under constant agitation in a fluidized-bed granulator with a paste which had been prepared by gelatinizing a 2.5 weight percent aqueous suspension of white potato starch at 85° C and cooling to 50° C, until the coating amount of white potato starch had reached 2 parts, followed by drying in situ. The product was then comminuted in a Fitz-mill equipped with a 1.5 mm-screen to obtain ascorbic acid granules.

b. To 510 parts of the granules prepared as above there were added 5 parts of magnesium stearate and 15 parts of corn starch, and after mixing, the composition was compressed into a 530 mg tablet.
L-ascorbic acid content: 94.3 weight percent
Hardness: 10.0 kg.
Tensile strength: 15.2 kg/cm²

EXAMPLE 3 a. 96 parts of ground powdery L-ascorbic acid which passed through a 200-mesh screen, 4.5 weight percent of which remained over a 250-mesh screen, but 82.8 weight percent of which passed through a 325-mesh screen were sprayed under constant agitation in a fluidized-bed granulator with a solution of 5.0 weight percent of hydroxypropylmethylcellulose until the coating amount of hydroxypropylmethylcellulose had reached 4 parts, followed by drying in situ to obtain L-ascorbic acid-containing granules.

b. to 520 parts of the granules prepared as above there were added 5 parts of magnesium stearate and 15 parts of corn starch, and after mixing, the composition was compressed into a 540 mg tablet.
L-ascorbic acid content: 92.6 weight percent
Hardness: 15.5 kg.
Tensile strength: 23.6 kg/cm²

EXAMPLE 4 a. 97 parts of ground powdery L-ascorbic acid which passed through a 200-mesh screen, 4.5 weight percent of which remained over a 250-mesh screen but 82.8 weight percent of which passed through a 325-mesh screen, were sprayed under constant agitation in a fluidized-bed granulator with a solution of 4.0 weight percent of ethylcellulose until the coating amount of ethylcellulose had reached 3 parts, followed by drying in situ to obtain L-ascorbic acid-containing granules.

EXAMPLE 5 a. L-ascorbic acid granules were obtained by the same manner as Example 4 (a), in which hydroxypropylmethyl-cellulose was used instead of ethyl cellulose.

b. 515 parts of the granules prepared as above (a) were compressed as the similar manner as Example 1, (b)-1 into a 535 mg. tablet.
L-ascorbic acid content: 93.5 weight percent
Hardness: 12.2 kg.
Tensile strength: 18.6 kg/cm²

EXAMPLE 6 a. 97 parts of ground powdery L-ascorbic acid which passed through a 200-mesh screen, 4.5 weight percent of which remained over a 250-mesh screen, but 82.8 weight percent of which passed through a 325-mesh screen, were sprayed under constant agitation in a fluidized-bed granulator with a paste which had been prepared by gelatinizing a 3.0 weight percent aqueous suspension of hydroxypropyl starch, which is described in Code of Federal Regulation Para. 121,1031, at 70° C and cooling to 50° C, until the coating amount of hydroxypropyl starch had reached 3 parts, followed by drying in situ. The product was then comminuted in a Fitz-mill provided with a 1.5 mm-screen to obtain L-ascorbic acid granules.

b. To 515 parts of the granules prepared as above there were added 5 parts of magnesium stearate and 15 parts of corn starch, and after mixing, the composition was compressed into a 535 mg tablet.

L-ascorbic acid content: 93.5 weight percent
Hardness: 12.3 Kg.
Tensile strength: 18.7 kg/cm$^2$

EXAMPLE 7 a. 96 parts of ground powdery L-ascorbic acid which passed through a 200-mesh screen, 4.5 weight percent of which remained over a 250-mesh screen, but 82.8 weight percent of which passed through a 325-mesh screen, were sprayed under constant agitation in a fluidized-bed granulator with a paste which had been prepared by gelatinizing a 5.0 weight percent aqueous suspension of corn starch at 85° C and cooling to 50° C, until the coating amount of starch had reached 4 parts, followed by drying in situ. The product was then comminuted in a Fitz-mill equipped with a 1.5 mm-screen to obtain L-ascorbic acid granules.

b. To 520 parts of the granules prepared as above there were added 5 parts of magnesium stearate and 15 parts of corn starch, and after mixing, the composition was compressed into a 545 mg. tablet.

L-ascorbic acid content: 92.6 weight percent
Hardness: 15.7 kg.
Tensile strength: 23.9 kg/cm$^2$

EXAMPLE 8 a. 96 parts of ground powdery L-ascorbic acid which passed through a 200-mesh screen, 4.5 weight percent of which remained over a 250-mesh screen, but 82.8 weight percent of which passed through a 325-mesh screen, were sprayed under constant agitation in a fluidized-bed granulator with a paste which had been prepared by gelatinizing an 8 weight percent aqueous suspension of pregelatinized modified starch, STA-RX 1500 (A. E. Staley Mfg. Co., U.S.A.) at 85° C and cooling to 50° C until the coating amount of the starch had reached 4 parts followed by drying in situ. The product was then comminuted in a Fitz-mill equipped with a 1.5 mm-screen to obtain L-ascorbic acid granules.

b. To 520 parts of the granules prepared as above there were added 5 parts of magnesium stearate and 1.5 parts of corn starch, and after mixing, the composition was compressed into a 540 mg. tablet.

L-ascorbic acid content: 92.6 weight percent
Hardness: 13.6 kg.
Tensile strength: 20.7 kg/cm$^2$

EXAMPLE 9 a. 98 parts of ground powdery L-ascorbic acid which passed through a 200-mesh screen, 4.5 weight percent of which remained over a 250-mesh screen, but 82.8 weight percent of which passed through a 325-mesh screen, were sprayed under constant agitation in a fluidized-bed granulator with a paste which had been prepared by gelatinizing a 5.0 weight percent aqueous suspension of corn starch at 85° C and cooling to 50° C until the coating amount of starch had reached 2 parts, followed by drying in situ. The product was then comminuted in a Fitz-mill equipped with a 1.0 mm-screen to obtain L-ascorbic acid granules.

b. To 510 parts of the granules prepared as above there were added 5 parts of magnesium stearate, and after mixing the composition was compressed into a 515 mg. tablet.

L-ascorbic acid content: 97.1 weight percent
Hardness: 8.9 kg.
Tensile strength: 13.6 kg/cm$^2$

TEST 1

A. METHOD i. 1. Preparation of granules a. Granules obtained by the present invention (ground powder was employed)

Granule (1) — granules obtained by Example 3 (a) (granules containing about 96% of L-ascorbic acid).
Granule (2) — granules obtained by Example 1 (a) (granules containing about 97% of L-ascorbic acid).
Granule (3) — granules obtained by Example 9 (a) (granules containing about 98% of L-ascorbic acid).

b. Granules obtained by the wet-granulation method (ground powder was employed)

Powdered L-ascorbic acid, which passed through a 200-mesh-screen, 4.5 percent of which remained over a 250-mesh screen and 82.8 percent of which passed through a 325-mesh screen, and pregelatinized starch, Amicol C (made by Nippon Starch Refining Co., Japan), were charged into the Pony Mixer, mixed well and 10 percent of water was added thereto, followed by massing. The resulting moistened powder is forced through a 3.0 mm-screen, and dried overnight at 40° C, and then comminuted in a Fitz-mill equipped with a 1.5 mm-screen.

Granule (4) — granules which contain about 90 percent of L-ascorbic acid.
Granule (5) — granules which contain about 95 percent of L-ascorbic acid.
Granule (6) — granules which contain about 97 percent of L-ascorbic acid.

i. 2. Preparation of Tablets.

The following tableting granules were compressed in a rotary tablet machine (RTM-S36-2S, made by Kikusui Seisakusho Co., Japan) to obtain 600 mgs. of tablet with 11.5 mm flat faced, beveled edged punchs and die.

| Tablets | Granules used | Calcium stearate | Silicon dioxide | Corn starch |
|---|---|---|---|---|
| (1) | Granule (2) | 1.0% | — | 5.0% |
| (2) | Granule (1) | 1.0% | — | 3.0% |
| (3) | Granule (2) | 1.0% | — | 3.0% |
| (4) | Granule (3) | 1.0% | — | 3.0% |
| (5) | Granule (3) | 1.0% | — | — |
| (6) | Granule (4) | 1.0% | 1.0% | 3.0% |
| (7) | Granule (4) | 1.0% | — | 3.0% |
| (8) | Granule (5) | 1.0% | 1.0% | 3.0% |
| (9) | Granule (5) | 1.0% | — | 3.0% |
| (10) | Granule (6) | 1.0% | 1.0% | 3.0% | ii. Tests of Strength of Tablets

Tablets (1) to (10) were compressed diametrically in a physical testing instrument (Autograph IS-5000, made by Shimazu Seisakusho Co., Japan) to measure their crushing strength. (See page 124 of Y. Yamaguchi and Y. Nishimatsu; Introduction to Rock Mechanics, University Press of Tokyo (1967)).

iii. DISINTEGRATION TEST

This was done according to the general test 31 disintegration test of Japanese Pharmacopoeia 8th Edition with the exception that in the present test an attached disk was not used and water was used as a solvent.

The requirement of the Japanese Pharmacopoeia is that the disintegration time of the tablet be no longer than 30 minutes.

(B) Results

| Tablet number | L-Ascorbic acid content % | Troubles in Tableting | Hardness (kg) | Tensile strength (kg/cm²) | Disintegration (minutes) |
| --- | --- | --- | --- | --- | --- |
| (1) | about 90.0 | No | 12.2 | 16.9 | 5.1 |
| (2) | about 92.3 | No | 16.0 | 22.2 | 28.0 |
| (3) | about 93.2 | No | 12.5 | 17.3 | 9.7 |
| (4) | about 94.1 | No | 9.6 | 13.3 | 4.1 |
| (5) | about 97.1 | No | 9.1 | 12.6 | 4.3 |
| (6) | about 86.4 | not free, following, sticking | 6.0 | 8.3 | 26.0 |
| (7) | about 87.3 | sticking | 5.7 | 7.9 | 26.1 |
| (8) | about 91.4 | sticking | 4.9 | 6.8 | 3.3 |
| (9) | about 90.5 | sticking, lamination | 4.1 | 5.7 | 3.5 |
| (10) | about 93.2 | sticking, lamination | 2.8 | 3.9 | 0.6 |

From the tests, the tablets in accordance with the process avoid the problems in tableting, exhibit high tensile strength and hardness and also exhibit excellent disintegration time.

What we claim is:

1. L-ascorbic acid granules produced by spray-coating L-ascorbic acid powder, having a size such that it passes through a 200-mesh screen, with a solution of a binder under constant agitation in a fluidized-bed granulating apparatus until the amount of the binder has reached about 2 to about 4 weight percent relative to the L-ascorbic acid.

2. L-ascorbic acid granules according to claim 1, wherein the binder is a water soluble or organic solvent-soluble binder.

3. L-ascorbic acid granules according to claim 2, wherein the binder is a water-soluble binder.

4. L-ascorbic acid granules according to claim 3, wherein the binder is selected from the group consisting of pregelatinized starch, pregelatinized modified starch, a water-soluble cellulose, polyvinyl pyrrolidone, polyvinyl alcohol, dextrin, gum arabicum and gelatin.

5. A method for producing L-ascorbic acid granules which comprises spray-coating L-ascorbic powder, having a size such that it passes through a 200-mesh screen, with a solution of a binder under constant agitation in a fluidized-bed granulating apparatus until the amount of the binder has reached about 2 to 4 weight percent relative to the L-ascorbic acid.

6. A method according to claim 5, wherein not lower than 50 weight percent of the L-ascorbic acid passes through a 325-mesh screen.

7. A method according to claim 5, wherein the concentration of the binder in the solution is about 1 to about 10 weight percent.

8. A method according to claim 5, wherein the binder is a water-soluble or organic solvent-soluble binder.

9. A method according to claim 8, wherein the binder is a water-soluble binder.

* * * * *